United States Patent
Latva-Käyrä et al.

(10) Patent No.: US 11,918,379 B2
(45) Date of Patent: Mar. 5, 2024

(54) WEARABLE SENSORS

(71) Applicant: Nokia Technologies Oy, Espoo (FI)

(72) Inventors: Tuomo Latva-Käyrä, Espoo (FI); Joni Jantunen, Helsinki (FI); Harri Lasarov, Espoo (FI); Leo Kärkkäinen, Helsinki (FI)

(73) Assignee: NOKIA TECHNOLOGIES OY, Espoo (FI)

( * ) Notice: Subject to any disclaimer, the term of this patent is extended or adjusted under 35 U.S.C. 154(b) by 1051 days.

(21) Appl. No.: 16/612,627

(22) PCT Filed: May 9, 2018

(86) PCT No.: PCT/FI2018/050348
§ 371 (c)(1),
(2) Date: Nov. 11, 2019

(87) PCT Pub. No.: WO2018/215692
PCT Pub. Date: Nov. 29, 2018

(65) Prior Publication Data
US 2020/0196951 A1 Jun. 25, 2020

(30) Foreign Application Priority Data
May 26, 2017 (EP) .................................. 17173142

(51) Int. Cl.
*A61B 5/00* (2006.01)
*A61B 5/024* (2006.01)
(Continued)

(52) U.S. Cl.
CPC ........ *A61B 5/6843* (2013.01); *A61B 5/02427* (2013.01); *A61B 5/0245* (2013.01);
(Continued)

(58) Field of Classification Search
None
See application file for complete search history.

(56) References Cited

U.S. PATENT DOCUMENTS 8,447,704 B2    5/2013   Tan et al.
9,483,123 B2   11/2016   Aleem et al.
(Continued)

FOREIGN PATENT DOCUMENTS

EP    3171248 A1       5/2017
JP    2009-195600 A    9/2009
(Continued)

OTHER PUBLICATIONS

Office action received for corresponding European Patent Application No. 17173142.5, dated Feb. 14, 2020, 9 pages.
(Continued)

*Primary Examiner* — Jay B Shah
(74) *Attorney, Agent, or Firm* — ALSTON & BIRD LLP

(57) ABSTRACT

An apparatus comprising: a controller configured to: receive one or more sensed signals from one or more wearable sensors, wherein a wearable sensor is for sensing a user's body and outputting a sensed signal dependent upon one or more biological processes of the user; process the one or more sensed signals and detect one or more bio signals that are determined by the one or more biological processes of the user; and process the one or more sensed signals to detect a user input signal indicative of: the user touching the user's body, and/or the user touching at least one of the wearable sensors, and/or relative movement of at least one of the wearable sensors relative to the user's body, and process the user input signal to identify a user input command.

16 Claims, 3 Drawing Sheets

(51) Int. Cl.
  *A61B 5/0245* (2006.01)
  *A61B 5/026* (2006.01)
  *A61B 5/0537* (2021.01)

(52) U.S. Cl.
  CPC .......... *A61B 5/0261* (2013.01); *A61B 5/0537* (2013.01); *A61B 5/4827* (2013.01); *A61B 5/6804* (2013.01)

(56) References Cited

U.S. PATENT DOCUMENTS

| | | |
|---|---|---|
| 2014/0364703 A1 | 12/2014 | Kim et al. |
| 2016/0091980 A1 | 3/2016 | Baranski et al. |
| 2016/0282947 A1 | 9/2016 | Schwarz et al. |
| 2016/0313801 A1 | 10/2016 | Wagner et al. |
| 2016/0374588 A1* | 12/2016 | Shariff ................ A61B 5/0533 600/547 |
| 2017/0147077 A1 | 5/2017 | Park et al. |

FOREIGN PATENT DOCUMENTS

| | | |
|---|---|---|
| JP | 2015-231550 A | 12/2015 |
| WO | 2017/007021 A1 | 1/2017 |

OTHER PUBLICATIONS

Tentative Rejection received for corresponding Taiwan Patent Application No. 107117942, dated Apr. 9, 2020, 7 pages of Tentative Rejection and 1 page of translation available.

Office action received for corresponding European Patent Application No. 17173142.5, dated Nov. 23, 2020, 6 pages.

Office action received for corresponding Japanese Patent Application No. 2019-565388, dated Dec. 3, 2020, 4 pages of office action and 5 pages of translation available.

Zhang et al., "Research on Gesture Definition and Electrode Placement in Pattern Recognition of Hand Gesture Action SEMG", International Conference on Medical Biometrics, 2008, pp. 33-40.

Extended European Search Report received for corresponding European Patent Application No. 17173142.5, dated Oct. 17, 2017, 9 pages.

International Search Report and Written Opinion received for corresponding Patent Cooperation Treaty Application No. PCT/FI2018/050348, dated Jul. 18, 2018, 13 pages.

Decision to Grant for Japanese Application No. 2019-565388 dated Aug. 3, 2021, 5 pages.

Notice of Allowance for Taiwanese Application No. 107117942 dated Aug. 31, 2020, 3 pages.

* cited by examiner

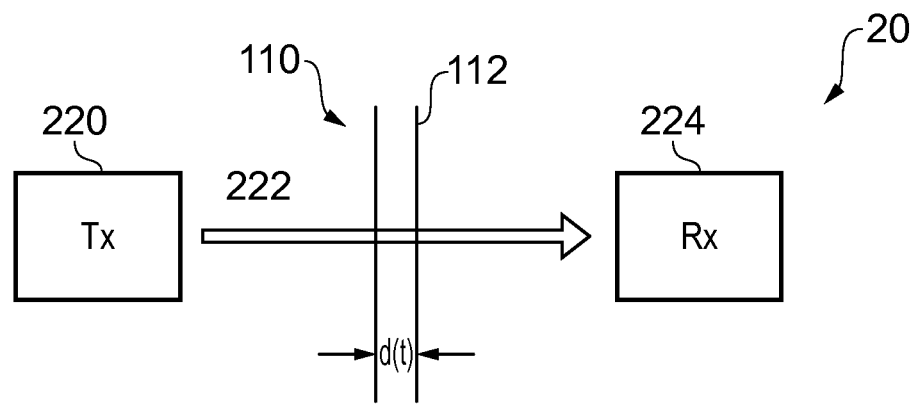
FIG. 7A
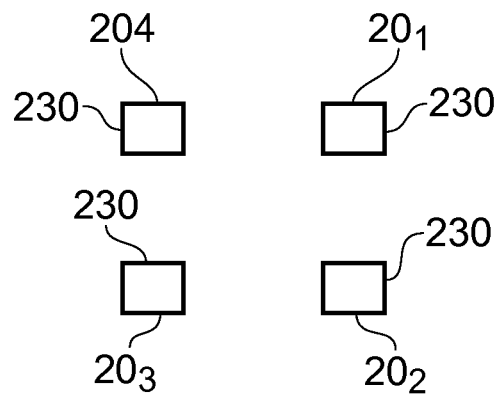
FIG. 7B
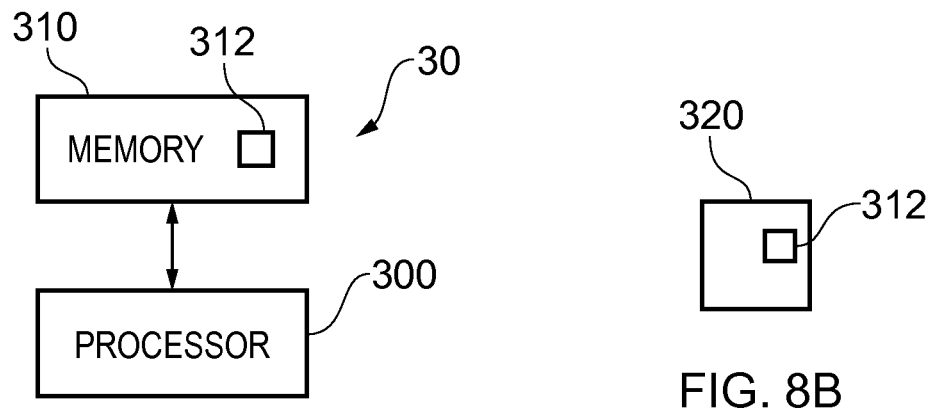
FIG. 8A
FIG. 8B

WEARABLE SENSORS

RELATED APPLICATION

This application was originally filed as PCT Application No. PCT/FI2018/050348 filed 9 May 2018 which claims priority benefit from EP Patent Application No. 17173142.5 filed May 26, 2017.

TECHNOLOGICAL FIELD

Embodiments of the present invention relate to wearable sensors. In particular, they relate to using wearable sensors in relation to apparatus, methods and computer programs.

BACKGROUND

Wearable sensors are sensors that can be worn by a person so that they travel with the person without being held in a person's hand, for example. Some wearable sensors may be attached to a person's body using a strap, adhesive or any other suitable attachment. Other wearable sensors may be integrated into something worn by the user, for example the user's clothes.

The wearable sensors may be used for different purposes. They may, for example, be motion or orientation sensors that record the movement of a user or record movement of a part of a user's body. Alternatively, or in addition, the wearable sensors may be bio signal sensors that are designed to sense the consequences of one or more biological processes of the user's body. Bio signal sensors may be used to monitor a physiological or pathological state of the user in a clinical, home, casual or sporting environment or elsewhere. In some circumstances bio signal sensors may be used to provide information to a user concerning aspects of their health such as pulse rate, blood pressure, blood oxygen levels, blood glucose levels etc.

The output of the bio signal sensors are processed to detect one or more bio signals that are determined by one or more biological processes of the user. There may be occasions when a user wishes to control the consequences of this processing, switch the processing on or switch the processing off or otherwise provide some form of user input command to the controller or apparatus performing the processing. This may, for example, be achieved by providing a user input interface to the controller for example via a screen and buttons at the wearable sensors or via a computer that is in communication with the wearable sensors.

BRIEF SUMMARY

According to various, but not necessarily all, embodiments of the invention there is provided an apparatus comprising:
a controller configured to:
receive one or more sensed signals from one or more wearable sensors, wherein a wearable sensor is for sensing a user's body and outputting a sensed signal dependent upon one or more biological processes of the user;
process the one or more sensed signals and detect one or more bio signals that are determined by the one or more biological processes of the user;
process the one or more sensed signals to detect a user input signal indicative of:
the user touching the user's body, and/or
the user touching at least one of the wearable sensors, and/or relative movement of at least one of the wearable sensors relative to the user's body, and
process the user input signal to identify a user input command.

According to various, but not necessarily all, embodiments of the invention there is provided a method comprising:
receiving one or more sensed signals from one or more wearable sensors, wherein a wearable sensor is for sensing a user's body and outputting a sensed signal dependent upon one or more biological processes of the user;
processing the received one or more sensed signals to detect one or more bio signals that are determined by the one or more biological processes of the user;
processing the received one or more sensed signals to detect a user input signal indicative of
the user touching the user's body, and/or
the user touching at least one of the wearable sensors, and/or
relative movement of at least one of the wearable sensors relative to the user's body, and
processing the user input signal to identify a user input command.

According to various, but not necessarily all, embodiments of the invention there is provided an apparatus comprising:
means for receiving one or more sensed signals from one or more wearable sensors, wherein a wearable sensor is for sensing a user's body and outputting a sensed signal dependent upon one or more biological processes of the user;
means for processing the received one or more sensed signals to detect one or more bio signals that are determined by the one or more biological processes of the user;
means for processing the received one or more sensed signals to detect a user input signal indicative of
the user touching the user's body, and/or
the user touching at least one of the wearable sensors, and/or
relative movement of at least one of the wearable sensors relative to the user's body, and
means for processing the user input signal to identify a user input command.

According to various, but not necessarily all, embodiments of the invention there is provided an apparatus comprising:
at least one processor; and
at least one memory including computer program code the at least one memory and the computer program code configured to, with the at least one processor, cause the apparatus at least to perform:
receiving one or more sensed signals from one or more wearable sensors, wherein a wearable sensor is for sensing a user's body and outputting a sensed signal dependent upon one or more biological processes of the user;
processing the one or more sensed signals and detect one or more bio signals that are determined by the one or more biological processes of the user; and
processing the one or more sensed signals to detect a user input signal indicative of
the user touching the user's body, and/or
the user touching at least one of the wearable sensors, and/or relative movement of at least one of the wearable sensors relative to the user's body, and processing the user input signal to identify a user input command.

According to various, but not necessarily all, embodiments of the invention there is provided a computer program that when run on a processor enables the performance of a method comprising:

receiving one or more sensed signals from one or more wearable sensors, wherein a wearable sensor is for sensing a user's body and outputting a sensed signal dependent upon one or more biological processes of the user;

processing the received one or more sensed signals to detect one or more bio signals that are determined by the one or more biological processes of the user;

processing the received one or more sensed signals to detect a user input signal indicative of the user touching the user's body, and/or the user touching at least one of the wearable sensors, and/or relative movement of at least one of the wearable sensors relative to the user's body, and processing the user input signal to identify a user input command.

According to various, but not necessarily all, embodiments of the invention there is provided an apparatus comprising:

a controller configured to:

receive one or more sensed signals from one or more wearable sensors, wherein a wearable sensor is for sensing a user's body and outputting a sensed signal dependent upon one or more biological processes of the user;

process the one or more sensed signals over a first period of time to detect the user input signal over the first period of time;

process the one or more sensed signals over the first period of time to remove from the one or more sensed signals, at least the detected user input signal over the first period of time, to enable detection of one or more bio signals over the first period of time that are determined by one or more biological processes of the user over the first period of time; and process the user input signal to identify a user input command.

According to various, but not necessarily all, embodiments of the invention there is provided a method comprising:

receiving one or more sensed signals from one or more wearable sensors, wherein a wearable sensor is for sensing a user's body and outputting a sensed signal dependent upon one or more biological processes of the user;

processing the received one or more sensed signals over a first period of time to detect the user input signal over the first period of time;

processing the received one or more sensed signals over the first period of time to remove from the one or more sensed signals, at least the detected user input signal over the first period of time, to enable detection of one or more bio signals over the first period of time that are determined by one or more biological processes of the user over the first period of time; and processing the received user input signal to identify a user input command.

According to various, but not necessarily all, embodiments of the invention there is provided an apparatus comprising:

means for receiving one or more sensed signals from one or more wearable sensors, wherein a wearable sensor is for sensing a user's body and outputting a sensed signal dependent upon one or more biological processes of the user;

means for processing the received one or more sensed signals over a first period of time to detect the user input signal over the first period of time means for processing the received one or more sensed signals over the first period of time to remove from the one or more sensed signals, at least the detected user input signal over the first period of time, to enable detection of one or more bio signals over the first period of time that are determined by one or more biological processes of the user over the first period of time; and means for processing the received user input signal to identify a user input command.

According to various, but not necessarily all, embodiments of the invention there is provided an apparatus comprising:

one or more wearable sensors, wherein a wearable sensor is for sensing a user's body and outputting a sensed signal dependent upon one or more biological processes of the user;

a controller configured to:

process the one or more sensed signals and detect one or more bio signals that are determined by the one or more biological processes of the user; and process the one or more sensed signals to detect a user input signal indicative of:

the user touching the user's body, and/or the user touching one or more of the one or more wearable sensors, and/or relative movement of one or more of the one or more wearable sensors relative to the user's body, and process the user input signal to identify a user input command.

According to various, but not necessarily all, embodiments of the invention there is provided examples as claimed in the appended claims.

BRIEF DESCRIPTION

For a better understanding of various examples that are useful for understanding the detailed description, reference will now be made by way of example only to the accompanying drawings in which:

According to various, but not necessarily all, embodiments of the invention there is provided FIG. 1 illustrates an example of an apparatus comprising one or more wearable sensors and a controller;

FIGS. 7A and 7B illustrate some examples of wearable sensors;

FIG. 8A illustrates an example of a controller;

FIG. 8B illustrates a computer program embodied in a delivery mechanism.

DETAILED DESCRIPTION

Figure 1:
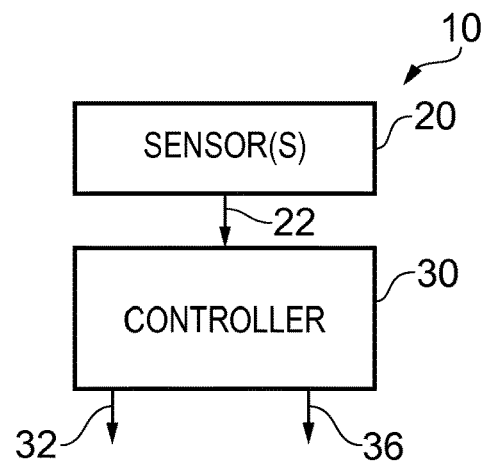

The figures referred to below describe an apparatus 10 comprising one or more wearable sensors 20 and a controller 30 configured to process one or more sensed signals 22 from the one or more wearable sensors 20 to identify a user input command 36, while also being capable of processing the one or more sensed signals 22 to detect one or more bio signals 32 that are determined by one or more biological processes of the user's body 110.

The apparatus 10 can therefore be positioned in or under a user's clothing and still be controlled. The apparatus 10 can be controlled by the user via interaction with the one or more wearable sensors 20 obviating the need for a user input interface other than via the one or more wearable sensors 20.

In some, but not necessarily all, examples, the user may enter a user input command 36 by directly interacting with the one or more wearable sensors 20 or directly interacting with the biological process sensed by the one or more wearable sensors 20. This may be achieved by, for example, the user touching the user's body 110 and/or the user touching one or more of the one or more wearable sensors 20 and/or by the user causing relative movement of one or more of the one or more wearable sensors 20 relative to the user's body 110.

In this way, the user by deliberately interfering with the sensing of the biological process by the one or more wearable sensors 20 enters a user input command 36.

In some, but not necessarily all, examples, the deliberate interference to the sensed signal 22 may be removed to recover a clean bio signal 32.

FIG. 1 illustrates an example of an apparatus 10 comprising one or more wearable sensors 20 and a controller 30. In some, but not necessarily all, examples, the one or more wearable sensors 20 and the controller 30 may be comprised within a single housing. In other examples, the one or more wearable sensors 20 and the controller 30 may be separate or separable. In some examples, one or more of the one or more wearable sensors 20 may be galvanically (direct current) connected to the controller 30, whereas in other examples one or more of the one or more wearable sensors 20 may be connected wirelessly to the controller 30.

A wearable sensor 20 is for sensing a user's body 110 (see FIG. 5A) and outputting a sensed signal 22 dependent upon one or more biological processes of the user's body 110.

The controller 30 is configured to process the one or more sensed signals 22 and detect one or more bio signals 32 that are determined by the one or more biological processes of the user's body 110. The controller 30 is also configured to process the one or more sensed signals 22 to detect a user input signal 34 and process the user input signal 34 to identify a user input command 36.

Bio signals 32 are determined by one or more biological processes of the user's body 110. These may, for example, be physiological processes (normal body processes) or pathological processes (abnormal body processes).

The user input command 36 is a command entered by the user that has the purpose of controlling the apparatus 10 or some other apparatus or process. It may, for example, control a state of a state machine controlled by the controller 30, annotate an event, acknowledge an alert, start/stop detection of further user input commands, start/stop further measurement of bio signals or perform any other suitable purpose.

In this example, but not necessarily all examples, the apparatus 10 has no other user input interface other than the wearable sensors 20. That is, the sole mechanism by which the user, when wearing the wearable sensors 20, can provide a user input command to the apparatus 10 is via the wearable sensors 20. In some, but not necessarily all, examples, there may be additional ports or machine interfaces that allow programming or control of the apparatus, for example, when it has been removed from the user's body. Therefore, in some examples, the apparatus 10 does not have a user input device such as a touch pad, touch screen, button, key, etc.

In some, but not necessarily all, examples, the controller 30 may be configured to provide a feedback signal to the user, for example, in the form of a tactile feedback (haptic feedback) signal or of an audio feedback (sound) signal. This feedback signal may, for example, be used as a confirmation signal to indicate that the apparatus 10 has successfully processed the one or more sensed signals 22 to identify a user input command 36. In some, but not necessarily all examples, the feedback signal may identify such a user input command 36 to the user.

Figure 2:
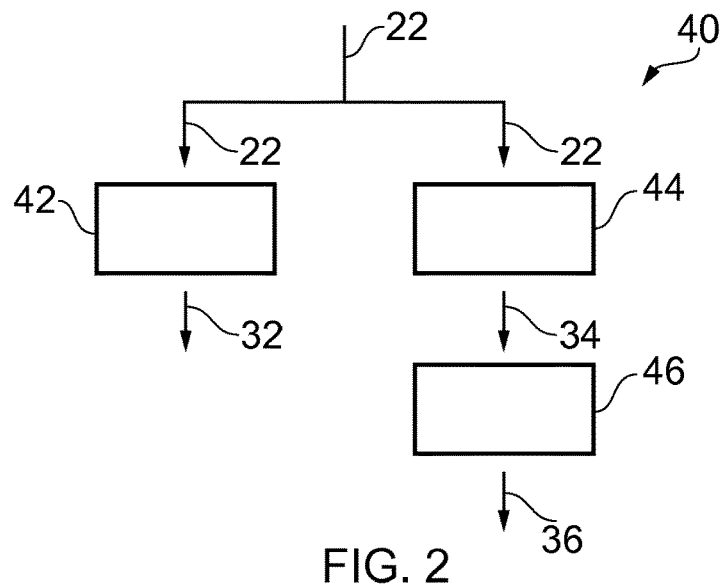
FIG. 2 illustrates an example of processing sensed signals.

FIG. 2 illustrates an example of the process 40 performed by one example of the apparatus 10 and, in particular, the controller 30. The controller 30 is configured to process 44 the one or more sensed signals 22 to detect a user input signal 34 indicative of the user 100 touching the user's body 110 and/or the user 100 touching one or more of the one or more wearable sensors 20 and/or relative movement of one or more of the one or more wearable sensors 20 relative to the user's body 110. The controller 30 is additionally configured to process 46 the user input signal 34 to identify the user input command 36.

In addition, the controller 30 is configured to process 42 the one or more sensed signals 22 and detect one or more bio signals 32 that are determined by the one or more biological processes of the user's body 110. The processing 42 may, or may not, occur before, after or simultaneously with the processing 44 and/or 46. That is, during one period of time, the controller 30 may perform only the processing 42 to produce one or more bio signals 32 and during a different period of time may not perform this processing but may instead perform the processing 44, 46 to produce the user input command 36. However, in other circumstances, the controller 30 may perform the process 42 for producing the one or more bio signals 32 simultaneously with the processes 44, 46 for producing the user input command 36.

Figure 3:
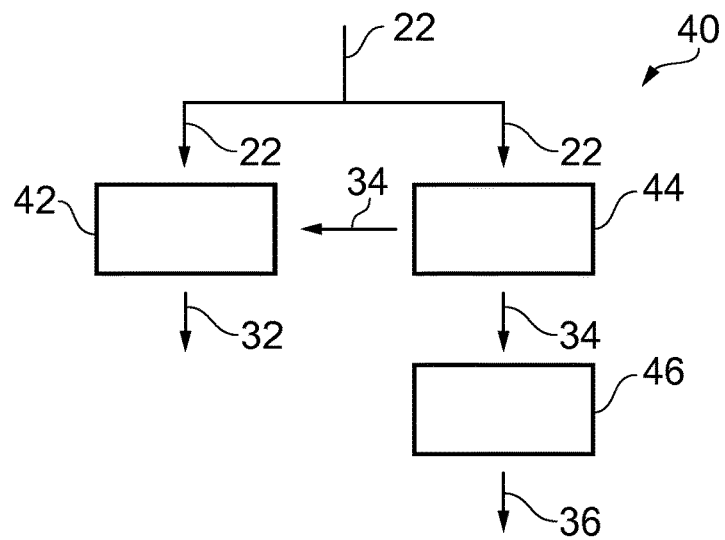
FIG. 3 illustrates an example of processing sensed signals.

FIG. 3 illustrates another example of the process 40 performed by one example of the apparatus 10 and, in particular, the controller 30. The controller 30 is configured to process 44 the one or more sensed signals 22 over a first period of time to detect a user input signal 34 indicative of the user 100 touching the user's body 110 and/or the user 100 touching one or more of the one or more wearable sensors 20 and/or relative movement of one or more of the one or more wearable sensors 20 relative to the user's body 110. The controller 30 is additionally configured to process 46 the user input signal 34 to identify the user input command 36.

In addition, the controller 30 is configured to process 42 the one or more sensed signals 22 and detect one or more bio signals 32 that are determined by the one or more biological processes of the user's body 110.

This process 42 comprises processing the one or more sensed signals 22 over the first period of time to remove from the one or more sensed signals 22, at least the detected user input signal 34 over the first period of time, to enable detection of one or more bio signals 32 over the first period of time that are determined by one or more biological processes of the user over the first period of time.

The processing 42 may, or may not, occur after or simultaneously with the processing 44 and/or 46.

In this way, the controller 30, is able to process the one or more sensed signals 22 to determine one or more bio signals 32 and a user input command 36. Artefacts in the one or more sensed signals 22, for example the user input signals 34 created by the user action performed to enter the user input command 36, are removed from the one or more sensed signals 22 to leave a cleaned-up bio signal 32, for bio signal processing.

Figure 4A:
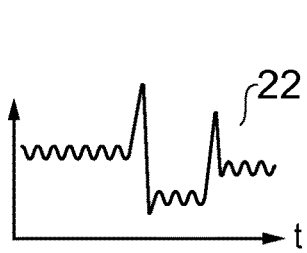
FIG. 4A is a schematic illustration of an example of a sensed signal.
Figure 4B:
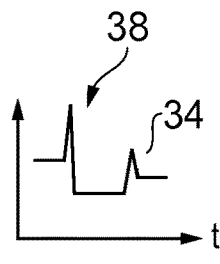
FIG. 4B is a schematic illustration of an example of a user input signal and FIG. 4C is a schematic illustration of an example of a bio signal.
Figure 4C:
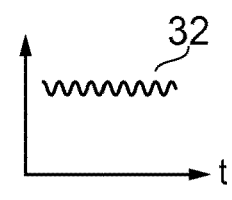

FIG. 4A is a schematic illustration of an example of a sensed signal 22. FIG. 4B is a schematic illustration of an example of a user input signal 34. FIG. 4C is a schematic illustration of an example of a bio signal 32.

The sensed signal 22 (FIG. 4A) may be considered to be formed from both the bio signal 32 (FIG. 4C) and an artefact signal 38 (FIG. 4B). In some examples, the artefact signal 38 may be the user input signal 34 only and in other examples there may be other additional artefacts not deliberately input or created by the user 100.

The sensed signal 22 may, for example, be processed by the controller 30 to detect the user input signal 34 illustrated in FIG. 4B, which is then subsequently processed to identify a user input command 36 (not illustrated). The controller 30 may also be configured to process the one or more sensed signals 22 illustrated in FIG. 4A to detect the one or more bio signals 32 illustrated in FIG. 4C.

Figure 5A:
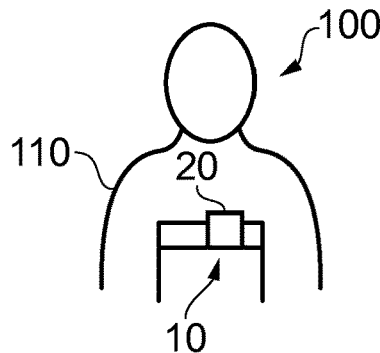
FIG. 5A illustrates an example in which a user, who is unclothed, is wearing one or more wearable sensors

FIG. 5A illustrates an example in which a user 100 is wearing the one or more wearable sensors 20. In this example, the user 100 is illustrated without clothes and the one or more wearable sensors 20 are adjacent the user's body 110. In this example, the one or more wearable sensors 20 and the controller 30 are both comprised in the apparatus 10 that is attached and worn by the user 100. In this example, the one or more wearable sensors 20 are attached directly to the user's body 110, in skin contact, at the thorax region and this is achieved, in this example, by means of a strap or belt. However, it should be appreciated that the one or more wearable sensors 20 may be positioned elsewhere on the user's body 110 at a position appropriate to the biological process of the user's body 110 that is being monitored.

Figure 5B:
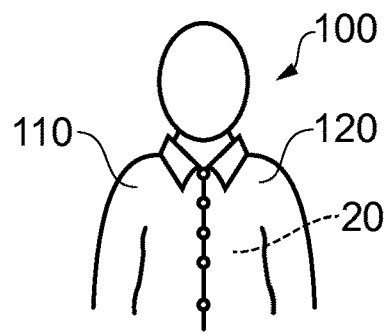
FIG. 5B illustrates the user, who is wearing one or more wearable sensors, clothed.

FIG. 5B illustrates the user 100 of FIG. 5A after they have placed clothes 120 over the body 110. The clothes 120 cover the apparatus 10, the one or more wearable sensors 20 and the controller 30. The clothes 120 therefore mediate when the user 100 touches the user's body 110 and/or when the user 100 touches one or more of the one or more wearable sensors 20 and/or when the user 100 causes relative movement of one or more of the one or more wearable sensors 20 relative to the user's body 110. That is, the user 100 is able to touch the user's body 110 and/or one or more of the one or more wearable sensors 20 without making physical contact with respectively the user's body 110 or the one or more wearable sensors 20.

Touching, in the sense used in this patent application, should not be interpreted as making direct physical contact although it does not exclude this possibility. It should instead be considered to be the application of a force, directly or indirectly, by a user's body 110.

Figure 6:
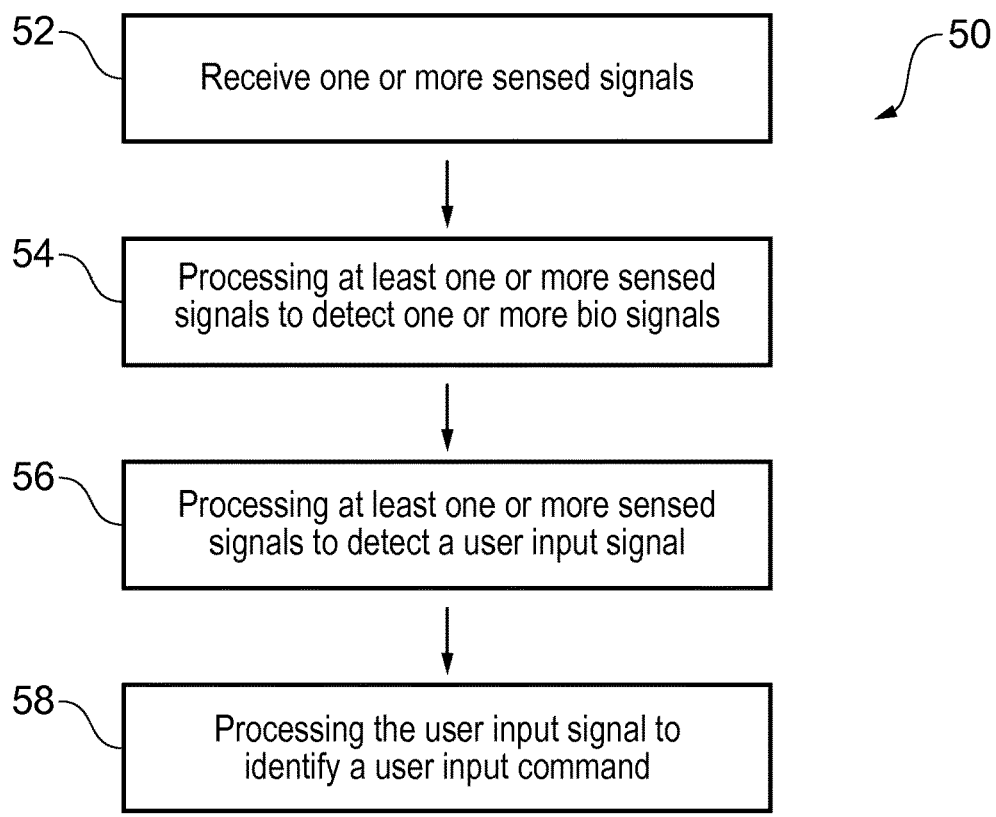
FIG. 6 illustrates an example of a method.

FIG. 6 illustrates an example of a method 50 comprising: at block 52 receiving one or more sensed signals 22 from one or more wearable sensors 20, wherein a wearable sensor 20 is for sensing a user's body 110 and outputting a sensed signal 22 dependent upon one or more biological processes of the user 100;

at block 54 processing the received one or more sensed signals 22 to detect one or more bio signals 32 that are determined by one or more biological processes of the user 100; at block 56 processing the received one or more sensed signals 22 to detect a user input signal 34; and at block 58 processing the user input signal 34 to identify a user input command 36.

In some, but not necessarily all, examples, block 56 comprises processing the received one or more sensed signals 22 to detect a user input signal 34 indicative of the user 100 touching the user's body 110 and/or the user 100 touching one or more of the one or more wearable sensors 20, and/or relative movement of the one or more of the one or more wearable sensors 20 relative to the user's body 110.

Additionally or alternatively, in some, but not necessarily all, examples, at block 54, processing the received one or more sensed signals 22 comprises processing the received one or more sensed signals 22 over a first period of time to remove from the one or more sensed signals 22, at least the detected user input signal 34 over the first period of time (and possibly other artefacts), to enable detection of one or more bio signals 32 over the first period of time that are determined by one or more biological processes of the user, for example, over the first period of time.

FIGS. 7A and 7B illustrate and the following paragraphs describe examples of suitable wearable sensors 20 which may each be used as the one or more wearable sensors 20, or which may be used in different permutations and combinations as the (multiple) wearable sensors 20. It should, however, be appreciated that other wearable sensors 20 may be used.

The wearable sensors 20 illustrated in these figures are non-invasive bio signal sensors 20. The bio signal sensors 20 are optimized and designed for the sensing of biological processes of the user's body 110. The biological processes may, for example, be physiological processes and/or pathological processes.

In some, but not necessarily all, examples, the bio signal sensors 20 may include passive sensors that detect signals produced by the user's body 110, such as, for example, electrical signals, pressure waves, volume changes. In some, but not necessarily all, examples, the bio signal sensors 20 may include active sensors that transmit and receive the transmitted signal after it has been modulated as a consequence of a biological process of the user's body 110, for example, the modulation of a transmitted optical signal by varying blood volume.

While in the above examples, an example of a passive sensor has been given as an electrical sensor, and an example of an active sensor has been given as an optical sensor, this is not necessarily always the case. Whether or not a bio signal sensor 20 is active or passive, the bio signal sensor 20 may be an electrical sensor and/or an optical sensor.

The volume of an organ of the user's body 110, for example the volume of blood, particularly arterial blood, may be a parameter that is useful to measure. It may, for example, be used to monitor heart function via pulse or pulse wave monitoring. It may also be useful for measuring a response of the user's circulation system, for example, to a stimulus such as a drug or posture change. A bio signal sensor 20 may therefore be a plethysmograph sensor that measures, for example, blood volume and in particular arterial blood volume. The plethysmograph sensor 20 may be an optical sensor.

Some biological processes cause or involve a flow of ions (ion current) in biological tissues), particularly at or near the skin. The bio signal sensor 20 may be an electrophysiology sensor 20 configured to detect a flow of ions (ion current) in biological tissues, for example at or near the skin.

The bio signal sensor 20 may for example be a bio-optical sensor. An example of a bio-optical sensor is a photoplethysmogram (PPG) sensor 20 that illuminates the skin and measures changes in light absorption. This may for example be used to monitor perfusion of blood to the dermis and subcutaneous tissues of the skin. FIG. 7A illustrates an example of such a bio-optical sensor 20. In this example, the bio-optical sensor 20 is arranged in a transmission configuration where light 222 produced by a light transmitter 220 passes through a portion of the user's body 110 to be received by a light receiver 224. However, in other examples, a reflection configuration may be used where light 222 produced by the light transmitter 220 is reflected by the user's body 110 and received by the light receiver 224. In a bio-optical sensor 20, a light transmitter 220 may be used with multiple light receivers 224 and/or a light receiver 224 may be used with multiple light transmitters 240. In some examples, different light transmitters 220 may be used at the same or different locations. The different light transmitters 220 may, for example, transmit light at different wavelengths. For example, red light and infrared light. Light emitting diodes may be used for light transmitters 220.

The absorption of the transmitted light 220 by the user's body 110 may be modelled according to the Beer-Lambert law. The optical absorption is dependent upon the optical path length through different media and the optical absorption coefficients of those media. In the illustrated example, blood vessels 112 are filled with blood. If these are venous blood vessels then they may be in a relatively steady state and if they are arterial blood vessels they may be pulsating having a variable diameter d(t).

The output of the light receiver 224 may be used as the sensor signal 22 or it may be processed before such use. It will be appreciated that with each arterial pulse wave, the volume of the arterial blood increases and this creates a measured variation in the sensed signal 22.

The sensed signal 22 may, however, also be affected by deliberate actions taken by the user 100. For example, if the user 100 touches the user's body 110 they may compress the area through which the transmitted light 222 passes, significantly reducing the path length which would cause a modulation of the sensed signal 22. Also, if the user 100 were to impede or restrict blood circulation locally this would change the extent to which the arterial pulse wave changes the volume of the blood vessels 112 and therefore also modulate the sensed signal 22. In some examples, it may even be possible for the user 100 to cause a variation in blood volume by tapping or pressing their body which would cause a modulation in the path length taken by the transmitted light 222 and therefore also modulate the sensed signal 22.

It will also be appreciated that the user 100 by touching one or more of the one or more wearable sensors 20 may compress the area between those sensors or otherwise change the length of the light path of the transmitted light 222 between the light transmitter 220 and the light receiver 224.

The light path of the transmitted light 222 from the light transmitter 220 to the light receiver 224 are be configured for the correct operation of the optical bio signal sensor 20. For example, it should not change during operation as changes will produce artefacts in the sensed signal 22. The user 100 may, however, deliberately create these artefacts by deliberately moving one or more of the wearable sensors 20 relative to the user's body 110. Moving the light transmitter 220 in effect moves the aperture of light transmission relative to an aperture of light reception at the receiver and moving the light receiver 224 moves the aperture of light reception. In some examples, it may be possible to detect not only that movement has occurred, but also the magnitude of the movement and the direction of the movement.

FIG. 7B illustrates an example of multiple bio signal sensors 20. In this example the bio signal sensors 20 are bio-electrical sensors, each comprising an electrode 230. The bio-electrical sensors 20 may for example be used as bio-potential sensors that are used to measure differential potential differences between the various sensors 20. For example, in the illustrated example each of the bio-electrical sensors $20_n$ has a different sub-script n that separately labels the different bio-electrical sensors 20. Each of the different bio-electrical sensors $20_n$ is located at a different position in electrical contact with the user's body 110. A potential difference $V_{nm}$ may be defined as the potential difference between the electrical potential at the bio-electrical sensor $20_n$ and the potential at the bio-electrical sensor $20_m$. In use, the bio-electrical sensors $20_n$ may have a fixed spatial configuration and variations in the potential differences $V_{nm}$ may be used, as an electrophysiology sensor, to detect flows of ions (ion currents) in biological tissues particularly at or near the skin.

One or more of the bio-electrical sensors 20 may be electrocardiography (ECG) sensors 20. Electrocardiography (ECG) sensors 20 measure the electrical activity of the heart over a period of time.

One or more of the bio-electrical sensors 20 may be impedance cardiography (ICG) sensors. Impedance cardiography (ICG) sensors 20 measure electrical conductivity of the thorax and its changes in time using bio-electrical electrodes 20 attached to the skin.

One or more of the bio-electrical sensors 20 may be electrodermal activity (EDA) sensors 20. Electrodermal activity (EDA) sensors 20 measure variations in the electrical characteristics of the skin e.g. galvanic skin response (GSR).

When the user 100 touches the user's body 110 then a direct or indirect current path may be established between one portion of the body 110 and another portion of the body 110 reducing electrical impedance between those portions. If the touch is via clothes, then the capacitance between the two portions of the body is increased as the separation between the portions of the user's body 110 decreases and when the user 100 makes physical contact between the two portions of the body then the electrical resistance between the two portions of the body may decrease significantly. The change in electrical impedance will cause a change in the electrical potentials at different portions of the user's body 110 which may be detected using the bio-electrical sensors 20.

Likewise, when the user 100 touches one or more of the one or more bio-electrical sensors 20, the potential difference between the touched one or more bio-electrical sensors 20 and the touching portion of the user's body 110 may change because the impedance between the sensor 20 and the touching portion of the user's body 110 has changed. The change in impedance may be a change in capacitance or resistance as explained above.

The spatial configuration of the bio-electrical sensors 20 may have a significant impact on the measured potential differences $V_{nm}$. As a consequence, a relatively small movement of one of the one or more bio-electrical sensors 20 relative to the user's body 110 and/or relative to other ones of the bio electrical sensors may modulate the sensed signal 22.

From the foregoing description, it will be appreciated that the controller 30 may be configured to process the one or more sensed signals 22 to detect a user input signal 34 by detecting a change in one or more measured parameters such as potential differences and/or blood volumes.

As explained above, potential differences and/or blood volumes may be modulated causing a modulation in the sensed signals 22 by the user 100 touching the user's body 110, the user 100 touching one or more of the one or more wearable sensors 20, the user 100 causing relative movement of one or more of the one or more wearable sensors 20 relative to the user's body 110. This therefore allows the user 100 to deliberately modulate the sensed signals 22 to encode the sensed signals 22 with information such as a user input command 36 or a sequence of user input commands 36 over time. The controller 30 may, for example, be configured to process the one or more sensed signals 22 to detect a user input signal 34 by detecting when one or more measured parameters create a predefined pattern. The user 100 may, for example, encode the sensed signals 22 with a user input command (or sequence of user input commands) 36 by deliberately modulating potential differences at the surface of the user's body 110 and/or blood volume at the surface of the user's body 110 over time.

The user 100 may therefore be able to input sophisticated commands to the controller 30. It may, for example, be possible for the user 100 to make a selection input command 36 and/or to make input commands similar to those made on the surface of a touch screen but instead using the surface of the user's body 110 such as one dimensional, one directional sliding inputs or two-dimensions and/or two directional tracing inputs.

The detection of the user input signals 34 within the sensed signals 22 may be achieved in a number of different ways. For example, in some, but not necessarily all, examples, the controller 30 may be configured to use a pattern-matching algorithm to detect within the sensed signals 22 predefined examples of the user input signals 34. This may be achieved in various different ways. In one example, a feature extraction engine may be used to extract features from the sensed signals 22 and the extracted features that relate to a particular user input command 36 may be identified (labelled). The labelled features may then be used in a machine learning model as a training input to produce a trained machine learning model. Examples of machine learning models include, for example, artificial neural networks and hidden Markov models. The trained machine learning model may then be used to process the sensed signals 22 automatically, without supervision, and identify the defined labels corresponding to the user input commands 36.

Referring back to FIGS. 4A, 4B and 4C, the sensed signal 22 may be considered to be the convolution of a bio signal 32 (FIG. 4C) and an artefact signal 38 (FIG. 4B). In some examples, the artefact signal 38 may be the user input signal 34 only and in other examples there may be other additional artefacts not deliberately input or created by the user 100. Knowledge of the expected artefact signal 38 including the expected user input signals 34 and knowledge of the general forms of the bio signal 32 allows the deconvolution of a received sensed signal 22 into an artefact signal 38 and a bio signal 32 and the processing of the artefact signal 38 to isolate the user input signal 34 or to recognize within the artefact signal 38 the existence of a user input signal 34 associated with a particular user input command 36. The controller 30 is therefore able to disambiguate the user 100 touching the user's body 110, the user 100 touching one or more of the one or more wearable sensors 20, the user 100 causing relative movement of one or more of the one or more wearable sensors 20 relative to the user's body 110 from changes to the sensed signal 22 caused by other factors such as for example caused by movement of the user's body 110 or the user's body muscles.

In some but not necessarily all examples, the controller 30 is able to disambiguate between the user 100 touching the user's body 110, the user 100 touching one or more of the one or more wearable sensors 20, and the user 100 causing relative movement of one or more of the one or more wearable sensors 20 relative to the user's body 110.

Implementation of a controller 30 may be as controller circuitry. The controller 30 may be implemented in hardware alone, have certain aspects in software including firmware alone or can be a combination of hardware and software (including firmware).

As illustrated in FIG. 8A the controller 30 may be implemented using instructions that enable hardware functionality, for example, by using executable instructions of a computer program 312 in a general-purpose or special-purpose processor 300 that may be stored on a computer readable storage medium (disk, memory etc) to be executed by such a processor 300.

The processor 300 is configured to read from and write to the memory 310. The processor 300 may also comprise an output interface via which data and/or commands are output by the processor 300 and an input interface via which data and/or commands are input to the processor 300.

The memory 310 stores a computer program 312 comprising computer program instructions (computer program code) that controls the operation of the apparatus 10 when loaded into the processor 300. The computer program instructions, of the computer program 312, provide the logic and routines that enables the apparatus to perform the methods illustrated in FIGS. 1 to 7B. The processor 300 by reading the memory 310 is able to load and execute the computer program 312.

The apparatus 10 therefore comprises:
at least one processor 300; and
at least one memory 310 including computer program code
the at least one memory 310 and the computer program code configured to, with the at least one processor 300, cause the apparatus 10 at least to perform:
receiving one or more sensed signals 22 from one or more wearable sensors 20, wherein a wearable sensor 20 is for sensing a user's body 110 and outputting a sensed signal 22 dependent upon one or more biological processes of the user 100;
processing the received one or more sensed signals 22 to detect one or more bio signals 32 that are determined by one or more biological processes of the user 100;
processing the received one or more sensed signals 22 to detect a user input signal 34;
and processing the user input signal 34 to identify a user input command 36.

In some, but not necessarily all, examples, the at least one memory 310 and the computer program code are configured to, with the at least one processor 300, cause the apparatus 10 at least to perform: processing the received one or more sensed signals 22 to detect a user input signal 34 indicative of the user 100 touching the user's body 110 and/or the user 100 touching one or more of the one or more wearable sensors 20, and/or relative movement of the one or more of the one or more wearable sensors 20 relative to the user's body 110.

Additionally or alternatively, in some, but not necessarily all, examples, the at least one memory 310 and the computer program code are configured to, with the at least one processor 300, cause the apparatus 10 at least to perform: processing the received one or more sensed signals 22 comprises processing the received one or more sensed signals 22 over a first period of time to remove from the one or more sensed signals 22, at least the detected user input signal 34 over the first period of time, to enable detection of one or more bio signals 32 over the first period of time that are determined by one or more biological processes of the user, for example, over the first period of time.

As illustrated in FIG. 8B, the computer program 312 may arrive at the apparatus 10 via any suitable delivery mechanism 320. The delivery mechanism 320 may be, for example, a non-transitory computer-readable storage medium, a computer program product, a memory device, a record medium such as a compact disc read-only memory (CD-ROM) or digital versatile disc (DVD), an article of manufacture that tangibly embodies the computer program 312. The delivery mechanism may be a signal configured to reliably transfer the computer program 312. The apparatus 10 may propagate or transmit the computer program 312 as a computer data signal.

Although the memory 310 is illustrated as a single component/circuitry it may be implemented as one or more separate components/circuitry some or all of which may be integrated/removable and/or may provide permanent/semi-permanent/dynamic/cached storage.

Although the processor 300 is illustrated as a single component/circuitry it may be implemented as one or more separate components/circuitry some or all of which may be integrated/removable. The processor 300 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/ software (including digital signal processor(s)), software, and memory(ies) that work together to cause an apparatus, such as a mobile phone or server, to perform various functions and
(c) to circuits, such as a microprocessor(s) or a portion of a microprocessor(s), that require software or firmware for operation, even if the software or firmware is not physically present. This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The blocks illustrated in the FIGS. 1 to 3 and 6 may represent steps in a method and/or sections of code in the computer program 312. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one" or by using "consisting".

One possible advantage of the various example embodiments described above is that user input commands can be provided to the apparatus even when one or more wearable sensors may not be directly accessible to a user for physical contact e.g. because they are covered by a user's clothes or because they are integrated within a user's clothes.

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An apparatus comprising:
at least one processor; and
at least one memory including computer program code;
the at least one memory including the computer program code configured to, with the at least one processor, cause the apparatus at least to perform:
receiving one or more sensed signals from one or more wearable sensors, wherein a wearable sensor is for sensing a user's body and outputting a sensed signal dependent upon one or more biological processes of the user;
processing the one or more sensed signals to detect one or more bio signals that are determined by the one or more biological processes of the user;
processing the one or more sensed signals to detect a user input signal indicative of the user touching at least one of the wearable sensors; and
processing the user input signal to identify a user input command;
wherein processing the one or more sensed signals comprises processing the one or more sensed signals over a first period of time to detect the user input signal over the first period of time; and
wherein processing the one or more sensed signals over the first period of time comprises processing the one or more sensed signals over the first period of time to remove from the one or more sensed signals at least the detected user input signal over the first period of time, prior to the detection of the one or more bio signals over the first period of time that are determined by the one or more biological processes of the user over the first period of time.

2. An apparatus as claimed in claim 1, wherein receiving one or more sensed signals from one or more wearable sensors comprises receiving one or more sensed signals from one or more wearable sensors that are configured to be worn by a user under a user's clothes.

3. An apparatus as claimed in claim 1, wherein receiving one or more sensed signals from one or more wearable sensors comprises receiving one or more sensed signals from one or more non-invasive bio signal sensors.

4. An apparatus as claimed in claim 1, wherein the one or more wearable sensors comprise a plurality of sensors, and wherein the at least one memory including the computer program code are configured to, with the at least one processor, cause the apparatus at least to perform: selecting at least one of the wearable sensors from a group comprising: passive bio signal sensors, active bio signal sensors, electrical bio signal sensors, optical bio signal sensors, plethysmograph sensors, and electrophysiology sensors.

5. An apparatus as claimed in claim 1, wherein receiving one or more sensed signals from one or more wearable sensors comprises receiving one or more sensed signals from one or more skin-contact electrodes.

6. An apparatus as claimed in claim 1, wherein the at least one memory including the computer program code are configured to, with the at least one processor, cause the apparatus at least to perform: processing the one or more sensed signals to detect a user input signal by detecting a change in one or more measured parameters selected from a group comprising: potential bio-electrical differences and potential blood volume differences.

7. An apparatus as claimed in claim 1, wherein the at least one memory including the computer program code are configured to, with the at least one processor, cause the apparatus at least to perform: processing the one or more sensed signals to detect a user input signal based on detecting a change in one or more measured parameters over time that corresponds to a predefined pattern.

8. An apparatus as claimed in claim 1, wherein the at least one memory including the computer program code are configured to, with the at least one processor, cause the apparatus at least to perform: disambiguation of the user touching at least one of the wearable sensors from changes to the sensed signal caused by movement of the user's body or user's body muscles.

9. An apparatus as claimed in claim 1, wherein the at least one memory including the computer program code are configured to, with the at least one processor, cause the apparatus at least to perform: processing the user input signal to identify a sequence of user input commands modulated onto the one or more bio signals by the user touching at least one of the wearable sensors.

10. An apparatus as claimed in claim 1, wherein the apparatus has no user input interface other than the one or more wearable sensors.

11. A method comprising:
receiving one or more sensed signals from one or more wearable sensors, wherein a wearable sensor is for sensing a user's body and outputting a sensed signal dependent upon one or more biological processes of the user;
processing the received one or more sensed signals to detect one or more bio signals that are determined by the one or more biological processes of the user;
processing the received one or more sensed signals to detect a user input signal indicative of
the user touching at least one of the wearable sensors; and
processing the user input signal to identify a user input command;
wherein processing the one or more sensed signals comprises processing the one or more sensed signals over a first period of time to detect the user input signal over the first period of time; and
wherein processing the one or more sensed signals over the first period of time comprises processing the one or more sensed signals over the first period of time to remove from the one or more sensed signals at least the detected user input signal over the first period of time, prior to the detection of the one or more bio signals over the first period of time that are determined by the one or more biological processes of the user over the first period of time.

12. A method as claimed in claim 11, wherein the one or more wearable sensors are configured to be worn by a user under a user's clothes.

13. A method as claimed in claim 11, wherein the one or more wearable sensors comprise a plurality of sensors, and wherein the method further comprises selecting at least one of the wearable sensors from a group comprising: passive bio signal sensors, active bio signal sensors, electrical bio signal sensors, optical bio signal sensors, plethysmograph sensors, and electrophysiology sensors.

14. A method as claimed in claim 11, wherein receiving one or more sensed signals from one or more wearable sensors comprises receiving one or more sensed signals from one or more skin-contact electrodes.

15. A method as claimed in claim 11, comprising processing the one or more sensed signals to detect a user input signal by detecting a change in one or more measured parameters selected from a group comprising: potential bio-electrical differences and potential blood volume differences.

16. A non-transitory computer readable medium comprising program instructions stored thereon for performing at least the following:
  receiving one or more sensed signals from one or more wearable sensors, wherein a wearable sensor is for sensing a user's body and outputting a sensed signal dependent upon one or more biological processes of the user;
  processing the received one or more sensed signals to detect one or more bio signals that are determined by the one or more biological processes of the user;
  processing the received one or more sensed signals to detect a user input signal indicative of
    the user touching at least one of the wearable sensors; and
  processing the user input signal to identify a user input command;
  wherein processing the one or more sensed signals comprises processing the one or more sensed signals over a first period of time to detect the user input signal over the first period of time; and
  wherein processing the one or more sensed signals over the first period of time comprises processing the one or more sensed signals over the first period of time to remove from the one or more sensed signals at least the detected user input signal over the first period of time, prior to the detection of the one or more bio signals over the first period of time that are determined by the one or more biological processes of the user over the first period of time.

* * * * *